United States Patent
Graf et al.

(10) Patent No.: US 11,872,153 B1
(45) Date of Patent: Jan. 16, 2024

(54) ORTHOPEDIC CASTING SLIPPER KIT AND METHOD

(71) Applicants: Peter M Graf, Mill Valley, CA (US); Richard M Stess, Mill Valley, CA (US)

(72) Inventors: Peter M Graf, Mill Valley, CA (US); Richard M Stess, Mill Valley, CA (US)

(*) Notice: Subject to any disclaimer, the term of this patent is extended or adjusted under 35 U.S.C. 154(b) by 0 days.

(21) Appl. No.: 18/318,092

(22) Filed: May 16, 2023

(51) Int. Cl.
*A61F 5/00* (2006.01)
*A61F 5/01* (2006.01)

(52) U.S. Cl.
CPC .................. *A61F 5/0127* (2013.01)

(58) Field of Classification Search
CPC .... A61F 5/0127; A61F 5/0109; A61F 5/0111; A61F 5/0113; A61F 5/0195; A61F 2013/00621; A61F 2013/00629; A61F 13/04; A61F 13/041; A61F 13/0064; A61F 13/066; A61F 13/067; A61F 2/5046; A61F 2002/5053; A61F 2002/5056; A61F 13/064; A61F 13/06; A61F 13/063; A61F 13/08; A43D 3/02; A43D 39/00
USPC ........................................................ 602/27
See application file for complete search history.

(56) References Cited

U.S. PATENT DOCUMENTS

| | | | | |
|---|---|---|---|---|
| 2,883,842 A | * | 4/1959 | Knohl | A61F 13/08 66/178 A |
| 4,817,590 A | * | 4/1989 | Stancik, Jr. | A61F 13/04 602/8 |
| 6,533,971 B1 | * | 3/2003 | Stess | B29C 33/3878 264/222 |
| 6,981,856 B2 | * | 1/2006 | Graf | B29D 35/14 264/223 |
| 2004/0226115 A1 | | 11/2004 | Gunnsteinsson | |
| 2005/0059919 A1 | * | 3/2005 | Farraday | A61F 2/80 623/36 |
| 2015/0025431 A1 | | 1/2015 | Linden | |

* cited by examiner

*Primary Examiner* — Adam Baker
(74) *Attorney, Agent, or Firm* — David S Dolberg

(57) ABSTRACT

An improved orthopedic casting slipper kit for custom molding of a foot casting, wherein the kit includes a low-cut casting slipper shaped to extend upwardly on a patient's foot from a plantar surface of the foot to an open end. and a quantity of curable resin for impregnation into the fabric of the casting slipper, the improvement comprising a sheer removal sock which is first placed on the patient's foot, prior to the casting slipper to facilitate removal of the hardened mold.

9 Claims, 2 Drawing Sheets

ORTHOPEDIC CASTING SLIPPER KIT AND METHOD

CROSS REFERENCE TO RELATED APPLICATIONS

This application provides an improvement to the invention disclosed in U.S. Pat. No. 6,981,856, which is incorporated herein in its entirety.

Technical Field

The present invention relates in general to kits and methods for making custom molded castings useful for the formation of orthopedic devices and orthotics. More particularly, the present invention relates to improved devices and methods of facilitating the removal of casted orthotic castings for the foot of the patient.

Background Art

Considerable effort has been directed toward the custom molding or formation of foot impression castings or casts which, in turn, may be used to form foot orthotic devices. Early approaches included the use of gauze strips and plaster of Paris to build up a casting or custom casting of the foot which, when hardened, was removed from the foot. A positive casting was made inside the hardened casting, and then the negative cast was removed, and the orthotic device made from the positive casting. This procedure was time-consuming, messy, somewhat inaccurate and the custom casting which was made was suitable only for making a single positive mold of the foot.

The gauze strip process was improved in a system shown in U.S. Pat. No. 2,593,742 to Friedman. In Friedman a slipper-shaped fabric casting form was substituted for the plurality of gauze strips to make the casting. The pre-shaped slipper form was impregnated with plaster of Paris, or some other material which is capable of hardening upon the application of water. Once hardened, the custom casting or casting of the foot was removed from the foot, and again, a positive was made inside the custom casting.

While the approach taken in Friedman reduced some of the messiness and handling problems, there were still substantial disadvantages. The Friedman pre-shaped slipper form only loosely fit the patient's foot, and when moistened with water, the operator had to press or fold the plaster of Paris containing cloth down against the foot, which was messy and created folds which detracted from the accuracy of the custom casting. Friedman also had the disadvantage of being capable of making only a single positive foot replica from the custom casting.

Various other custom casting kits are also found in the patent literature. Most of these kits are based upon the use of strips of fabric material or moldable surfaces against which the foot can be held. Typical of these prior art devices are the kits or casting systems disclosed in U.S. Pat. Nos. 1,647,639; 2,136,815; 2,856,663; 2,894,288; 2,907,067; 2,952,082; 2,955,326; 2,964,714; 3,320,347.

A commercially available moldable surface system for making orthotics is the BIO-FOAM System produced by Smithers Bio-Medical Systems of Kent, Ohio. The BIO-FOAM system is based upon a foam material into which the patient presses his or her foot. The foam deforms to the shape of the plantar surface of the foot, and the deformed foam can be used to make a positive plaster cast of the plantar surface. Casting the arch using the BIO-FOAM system can cause problems in that pushing down on the foam to deform it tends to flatten the arch. Shipping the deformed foam cast from the technician taking the casting to the laboratory making the positive cast also can result in damage to the deformed foam casting.

More recently, water-hardenable resins have been used in connection with knit fabric material to produce a variety of custom casting products. Typical of such resin-based custom casting systems are the kits set forth in U.S. Pat. No. 5,228,164 for the preparation of a custom last for preparing footwear, and U.S. Pat. No. 6,533,971 for the preparation of an orthopedic casting shirt, both of which contain technology useful in the present invention, and accordingly, are incorporated by reference into this application.

In U.S. Pat. No. 5,228,164, an elastic casting sleeve, or tubular shell-forming fabric member, is employed which can be slipped over the patient's foot and has sufficient extensibility and resilience to conform to the foot and present a smooth exterior surface which permits the hardened sleeve to act as a shell for the preparation of custom footwear. The sleeve contains or may have resin added to it which is water activatable so as to harden in a short period of time while on the patient's foot. The hardened sleeve can then be cut off the foot, and it is sufficiently thin and smooth so as to enable its use as a positive casting for the formation of custom footwear over the outside of the hardened sleeve. The interior of the sleeve can also be used to form positive castings in a conventional manner.

It has been found, however, that the use of such casting sleeves for the formation of orthotics that engage primarily the plantar surface of the foot is not very practical. The prior art casting sleeve comes up undesirably high on the patient's foot, and there is a tendency for the elasticity of the fabric to cause the sleeve to "bridge" or "tent" in the area of the arch of the foot. Since orthotics often are designed to provide arch support, such bridging or tenting is highly undesirable.

U.S. Pat. No. 6,981,856, upon which the current application is based, provides an orthopedic casting slipper and corresponding kit, the slipper comprising a resilient fabric casting slipper that extends only from the plantar aspect of a patient's foot to below the foot's dorsum, a longitudinal resiliently extensible band proximate to the open end, and an arch strap that spans transversely other the foot dorsum to snug the slipper into contact with the foot arch to prevent bridging. The kit includes the casting slipper, resin, and a barrier envelope that prevents adherence of the resin to the patient's foot, but does not include a removal sock.

However, removal of the hardened cast has proven somewhat difficult due to the friction and vacuum suction (See Method in Specification) between the foot and the barrier envelope, requiring two hands of the technician to shift and slide the mold while the patient wiggles their toes.

Specification of the Invention

Generally, two types of casts are known in the art. The first is a therapeutic cast, configured to immobilize or restrict mobility of a limb or joint of a subject. A therapeutic cast is designed to be left in place for an extended period of time to promote healing. The second is an impression cast configured to be molded to and reflect the external contour of the body part upon which the impression cast is placed. Once hardened, the impression cast is removed for further processing. The invention provided herein is related to impression casts, impression casting and kits comprising the components for impression casting.

Accordingly, it is an object of the present invention to provide an orthotic impression casting slipper kit 21 with a removal sock 60, which is first placed around the patient's foot 27 and located between the patient's foot and the barrier envelope 45 that is subsequently placed over the removal sock 60. The casting slipper 23 placed over the barrier envelope 45. Once hardened, the removal sock 60 provides a low coefficient of friction and inhibits vacuum suction between the foot, and the barrier envelope 45.

A further object of the present invention is to provide a method of using orthopedic casting slipper kit 21 that includes the removal sock 60 to make an impression mold of a patient's foot, and significantly improve the ease of removal of the hardened cast from the foot of the patient.

The orthotic casting slipper kit that includes the removal sock, and methods of using the present invention and other objects and features of advantage which will become apparent from, or are set forth in more detail in the Specification and accompanying drawings.

As shown in FIG. 1, the improvement, which is the focus of the present invention is the addition of a diaphanous fabric removal sock 60 with a low coefficient of friction between itself and the hardened orthopedic casting slipper kit, and which in the method of casting, is first fitted upon the foot of the patient. The material most suited for the removal sock 60 is nylon, however other synthetic fibers including acrylic, polyester, polypropylene and rayon maybe adapted for this purpose. When placed on the foot, the removal sock is ultra-sheer or sheer with a denier of 1 to 100, preferably with a denier of 10 to 30, and more preferably about 20, equivalent to –0.0.01 inch (0.25 mm). In an embodiment, the removal sock 60 is fabricated to conform to the shape of a foot 27, and extends from plantar aspect or surface 29 of the patient's foot up the lower extremity of the leg 31 to a position beyond the dorsum 30 of the foot, and as well, beyond the top of the casting slipper 33 (described below). The upper end of the removal sock is open at 36 to allow the patient to easily slip the sock onto foot.

As shown in FIG. 2, the orthopedic casting slipper kit 21 of the present invention comprises a resilient fabric casting slipper 23, which when positioned on a patient's foot 27, extends upwardly from a plantar surface to an opened end proximate the patient's instep. The slipper fabric is sufficiently resilient to substantially conform to the patient's foot, and a resilient, longitudinally extensible band is provided on the slipper proximate the opened end, and the band is formed to hold the opened end snugly against the patient's instep and heel. The kit also includes a quantity of curable resin 25 sufficient to harden the casting slipper into a hardened cast foot casting. Preferably the resin is impregnated into the fabric of the casting slipper and the slipper and curable resin are stored in a resin-impervious, airtight pouch. Alternatively, the resin may be provided in a container 28 separate from the casting slipper.

In an embodiment, the kit further includes an arch strap 39, which is fixably or removably attached to the medial side of the casting slipper proximate to the open end 36, and dimensioned to span transversely across the dorsum of the patient's foot, spanning the opened end to the lateral side of the casting slipper where it is removably attachable proximate to the open end 36. The arch strap is intended to enable the technician to pull the casting slipper up into contact with the patient's arch.

The method of creating a custom molded foot casting of the present invention is comprised, briefly, of the steps of first mounting a sheer removal sock 60 on the patient's foot 27 and leg 31, followed by a plastic barrier envelope 45 placed over the removal sock and intended to provide a barrier between the resin in the casting slipper and the removal sock. Then the elastic casting slipper 23 (preferably resin impregnated) is placed over the barrier envelope on the patient's foot, the slipper preferably having an arch strap 39 attached to a medial side of the slipper; pulling the slipper up into contact with the patient's arch; while the slipper is in contact with the patient's arch, fastening the arch strap to the opposite, lateral side of the slipper to maintain the slipper in contact with the patient's arch; manipulating the patient's foot to achieve a desired orientation; and hardening the resin in the slipper while the patient's foot is in the desired orientation. Once the resin is hardened the casting slipper is easily removed from the patient's foot due to the low coefficient of friction and the absence of vacuum suction between the barrier envelope, and the sheer removal sock.

Figure 1:
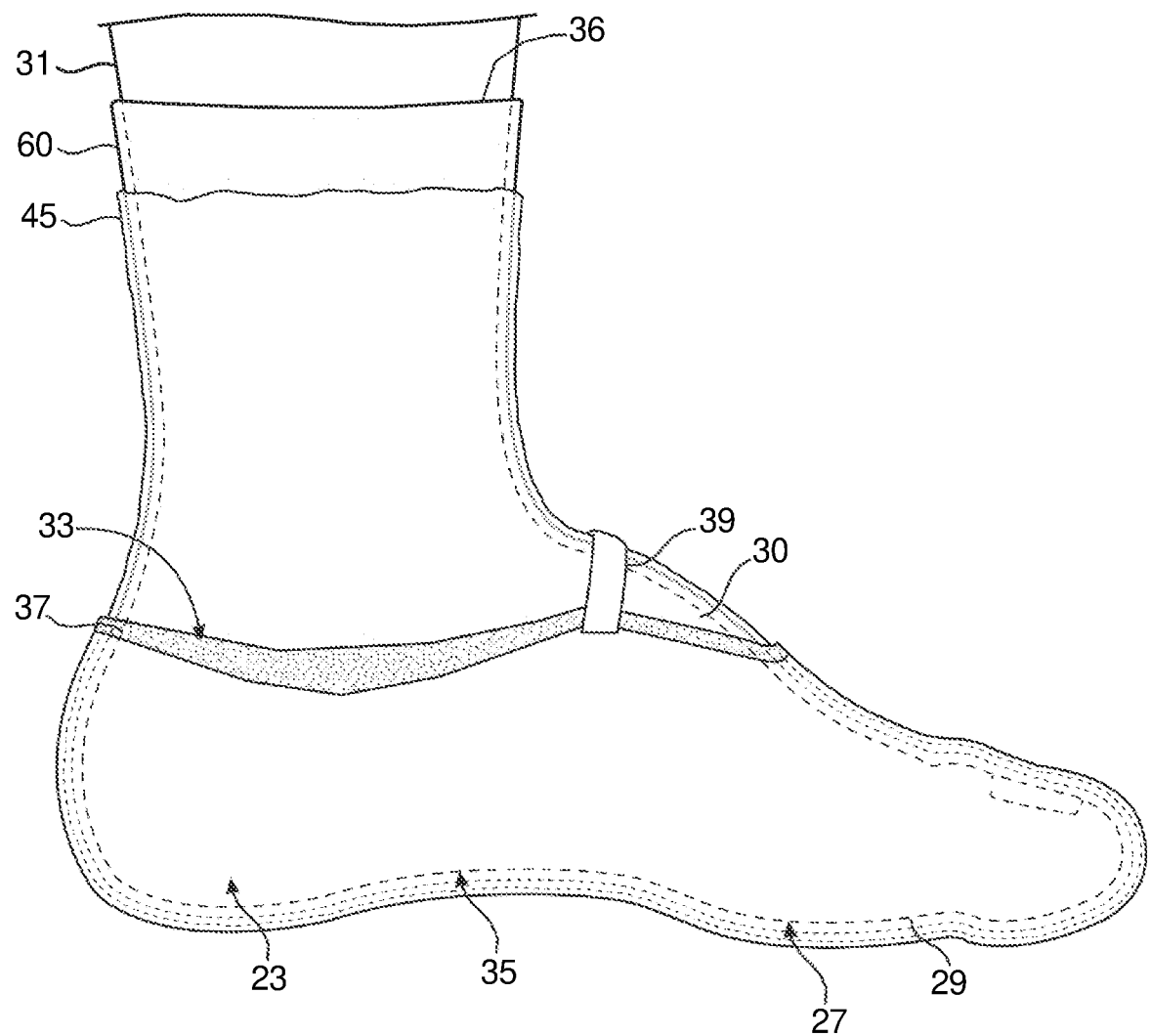
FIG. 1 is a medial side elevation of the casting slipper snugged up against the patient's arch.

Reference will now be made in detail to the kit and method of use of the present invention, an example of which is illustrated in the accompanying drawings. While the invention will be described in conjunction with a preferred embodiment, it will be understood that it is not intended to limit the invention to that embodiment. On the contrary, the invention is intended to cover alternatives, modifications and equivalents which may be included within the spirit and scope of the invention as defined by the appended claims.

The orthopedic casting slipper kit, generally designated 21, of the present invention includes a resilient fabric casting slipper 23 and a quantity of curable resin 25 sufficient to harden the casting slipper into an accurate impression of a patient's foot 27 and particularly the plantar surface 29 thereof. Casting slipper 23 has the shape of a relatively low-cut slipper and it extends from plantar aspect or surface 29 of the patient's foot up to a position near the dorsum 30 of the foot. The upper end of the slipper is open at 33 to allow the patient to easily slip the slipper onto foot and after it has hardened, to enable its removal, which is an important feature that will be described below.

The kit disclosed herein features the improvement, namely a sheer fabric removal sock 60 which is first placed on the foot 27 of the patient as the first step in the method. The sheer slick material of the removal sock 60 provides low coefficient of friction between the foot and the hardened casting slipper and retards formation of a vacuum during smoothing and pressing of the resin-impregnated casting slipper onto the foot, thereby facilitating superior subsequent removal of the slipper from the foot once the resin has hardened.

A plastic barrier envelope 45 is then placed over the removal sock so that the resin 25 does not adhere to the removal sock or the patient's foot during hardening. Such a flexible plastic barrier envelope can have a very thin wall thickness, for example, it can be provided as 0.002 inch thick. polyethylene or a similar very thin film.

The fabric casting slipper 23 is pre-formed in a slipper shape, as is true of the casting form of Friedman. Pat. No. 2,593,742, but unlike Friedman, the fabric material in the casting slipper of the present invention is both elastic and resilient so as to substantially conform to the patient's foot.

Thus, the folds which can result from the use of flexible but non-resilient gauze-like material are not present. The material which is most suited for use in slipper 23 is an elastic knit fabric, such as polyester or a polyester-spandex combination, or a fabric as set forth in U.S. Pat. No. 5,228,164. However, the elasticity of such fabrics, as used in the present invention, also tend to cause them to tent or bridge across arch 35 of the foot.

Accordingly, in an embodiment, the casting slipper 23 of the present invention is further provided with a resilient band 37 provided on slipper 23 proximate to the opened end 33. Resilient band 37 is formed to resiliently contract along its length so as to hold opened end 33 of slipper snuggly against the dorsum and heel of the patient's foot. As shown in FIG. 1, the resilient band 37 encircles the patient's foot 27 at the ankle so as to augment the resiliency in the slipper fabric, and so as to create improved overall conformance of the casting slipper to the patient's foot. The resilient band 37 also will tend to pull the casting slipper upwardly along the leg so as to reduce somewhat the tendency for tenting or bridging of slipper 23 in the area of the arch 35. The band 37 can be formed in any suitable manner. In one embodiment, band 37 includes a strip of elastic or extensible material that is integrated into the material of slipper 23, for example by being folded over the upper edge of fabric slipper 23 and enclosed within stitching secured to the slipper. In another embodiment, band 37 can be formed as a compression cuff, such as a fashioned compression cuff, provided proximate opened end 33, or by any other suitable means. In a further embodiment, band 37 can include a string or similar elongate member slidably disposed in a channel or sleeve formed around the opening 33 of the fabric slipper, with the two ends of the string extending out of respective openings provided in the sleeve so as to permit the string to be drawn taught within the sleeve and around the opened end of the slipper and the two ends of the string tied together to retain the string in its taught position.

In a preferred embodiment, four to five sizes of resilient casting or casting slippers will be made available to the technician to cover the normal foot sizes for an average patient population, namely, small, medium, large, and extra-large (and extra-extra-large if needed). This minimizes the likelihood of a loose fit of the casting slipper, and ensures a higher degree of conformance than can be achieved by only relying on the resiliency in the fabric itself. Conversely, providing multiple sizes reduces the likelihood of a tight fit, which would create a greater tendency for the slipper to bridge across the arch 35 due to fabric resiliency.

In order to obtain even better conformance of casting slipper 23 to foot 27, in an embodiment, an arch strap 39 is provided, which is dimensioned to transversely span over the dorsum 30 of the foot and across open end 33 of the casting slipper. Arch strap 39 may be fixably or removably secured at the medial side of the casting slipper proximate to the open end 33 above the arch 35, and the other end removably affixable to the lateral side of the slipper.

The arch strap 39 is preferably provided as an elastic band, for example a length of surgical tubing, with hooks at either end, fabricated to engage with the resilient band 37 in a removably fixable manner. It can also be provided by a strap which is permanently secured, for example by sewing, to one location of the slipper, for example to the medial side of the casting slipper, and releasably securable to the other lateral side of the slipper. Hook-and-loop fastener assemblies are commercially distributed under the trademark VELCRO, and a band of the hooks portion of such fastener assemblies is well suited for hooking to a knit fabric slipper.

It will be understood that other types of fasteners could be employed, such as snaps, clips, buttons, etc. Additionally, the arch strap 39 could be resilient or elastic and sewn to both sides of the slipper, but an elastic strap could require scissors to remove and might not be able to attain the conformance that would be otherwise desirable.

Figure 2:
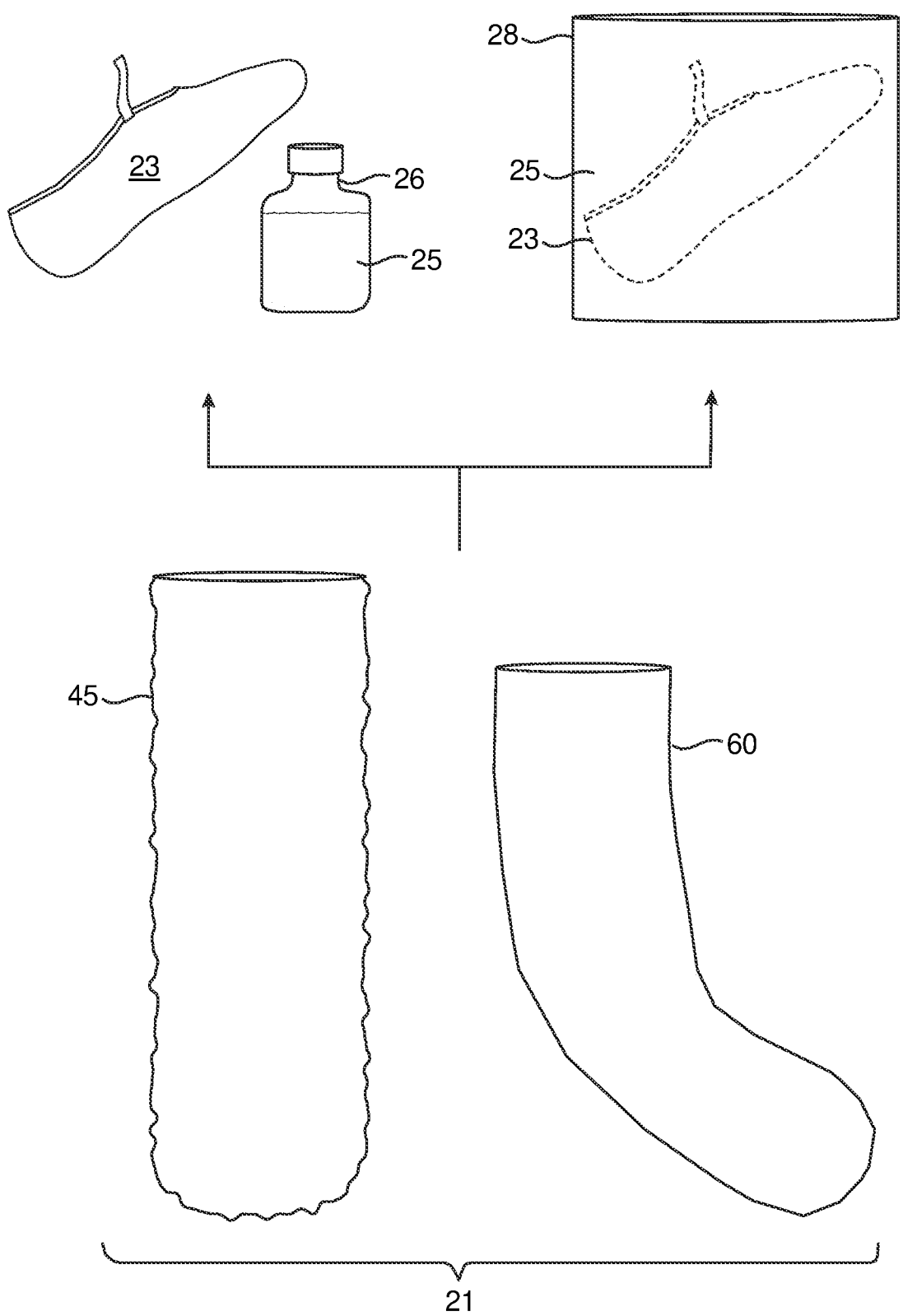
FIG. 2 depicts an orthopedic casting kit comprising a removal sock, a barrier envelope, and either a dry casting slipper with resin provided in a separate container, or the casting slipper in a pouch containing resin.

Resin 25 suitable for use with the slipper-shaped casting fabric form 23 can preferably be a water-hardenable resin, such as a polyurethane resin of the type disclosed in U.S. Pat. Nos. 5,228,164 and 6,981,856 (incorporated herein by reference), each with the same co-inventors as this application. As shown in FIG. 2, the resin 25 is previously impregnated into the casting slipper 23 and provided in a closed pouch or envelope 28 (preferable), or it can be provided in a separate container 26. If a separate resin container 26 is used, the casting slipper 23 can be provided in open air with resin 25 being subsequently added to the dry casting slipper immediately before placing the slipper on the patient's foot, or after it has been placed on the patient's foot. Having described the components of the orthopedic casting slipper kit of the present invention, it's use and the method of the present invention can be described.

Method

As a first step, a sheer removal sock 60 is placed on the foot 27 of the patient and pulled up along the leg 31.

As a second step, a plastic barrier envelope 45 is placed over the removal sock such that the resin 25 will not adhere to the removal sock or the patient's foot during hardening. Such flexible plastic barrier envelope preferably has a very thin wall thickness, for example, it can be provided as 0.002 inch thick. polyethylene or a similar very thin film.

Next, the resilient casting slipper 23 is placed over the barrier envelope on the patient's foot 27. As previously described, this step can be accomplished either by providing the curable resin already impregnated in the casting slipper (preferred), or mounting the dry casting slipper on the patient's foot and then impregnating the fabric with resin. The strap 39 is preferably attached to the slipper, and preferably affixed to the medial side of the slipper. The casting slipper preferably has an elastic band 37 that snugs the slipper down against the foot over the barrier envelope 45 into good conformance with the shape of foot 27, particularly the plantar surface 29.

When provided in an embodiment, the slipper is then pulled up into contact with the patient's arch by using arch strap 39. This enhances arch conformance. With the slipper in contact with the patient's arch, the arch strap 39, is affixed to the resilient band 37 at the medial side of the foot, proximate to the apex of the arch. The arch strap 39 is then stretched over the dorsum of the patient's foot, and fastened to the resilient band 37 at lateral side of the slipper so as to maintain the fabric casting slipper 23 in contact with arch 35 of the foot. The technician, podiatrist, orthotist, prosthetist, pedorthist, or orthopedic shoe technician can then smooth or ease the resin impregnated slipper on the patient's foot to further assist in conformance and to remove any wrinkles and thereafter manipulate the patient's foot to achieve a desired orientation. This smoothing and easing process invariably removes air from between the foot and the barrier thus creating a slight vacuum when the resin dries. This vacuum retards the removal of the hardened casting slipper from the patient's foot. Addition of the removal sock in the present invention minimizes vacuum formation. The resin in the slipper is hardened while the patient's foot is in the desired orientation.

The technician then manipulates the foot to place the foot in the "neutral" position (one-third of the distance from full pronation to full supination). An upward pressure on the fore-foot is one way to lock the bones in a semi-weight bearing neutral position, but other casting positions can also be employed, in the judgment of the technician.

Preferably, hardening of the resin will be accomplished by spraying water on the slipper 23 while on the patient's foot. Alternatively, the slipper may be dipped in water prior to application to the foot to begin activation of the resin hardening process. Hardening typically requires 2 or 3 minutes to reach a sufficiently hard state to enable removal of the cast slipper. The relatively rapid hardening of the water-activatable resin also minimizes the time during which the patient must maintain his foot in a desired orientation while the custom casting sets up.

Once the casting slipper has hardened, it is removed from the patient's foot by first releasing the arch strap. Due to the low coefficient of friction and absence of a vacuum between the removal sock and the barrier envelope, the technician can then pull gently down in the area of the back of the heel and slide the slipper forward off the foot. The relatively low-cut position of open end 33 on the dorsum will facilitate removal of hardened slipper 23 without the need for cutting of the casting slipper.

The hardened slipper casting can then be sent to a separate lab for formation of a foot orthotic from the hardened slipper, through scanning or formation of positives. The same slipper can be used to form a plurality of positive casts since the hardened resin and fabric will not be destroyed, as is the case with plaster of Paris casts, if the slipper is cut to release the positive. To release a positive cast from the hardened casting slipper 23, the positive cast may be cut by making a first downward cut in the area of the back of the heel to the plantar aspect 29 of the heel and a second cut starting proximate the anterior opening of the slipper directed toward the middle toe area. The hardened slipper can then be bent in medial and lateral directions outwardly to release a hardened positive casting inside the slipper. It is a simple matter to bend the hardened slipper back together and secure it for manufacture of subsequent positive casts.

Although the orthopedic casting slipper kit of the present invention has been described with one arch strap 39, in another embodiment the slipper kit can be provided with no arch strap or one or more arch straps for attachment to the slipper at other locations than the one described above with respect to strap 39. For example, any suitable strap (not shown) can be attached at each end to the rear of slipper proximate to the opened end 33 and extended over the dorsum 30, and can be used in conjunction with or as an alternative to strap 39.

What is claimed is:

1. An orthopedic impression casting slipper kit for custom molding of a patient's foot comprising:
   a. a fabric casting slipper configured for placement over a barrier envelope around the patient's foot and shaped to extend upwardly from the plantar surface of the patient's foot to an open end of the casting slipper proximate to the dorsal surface of the foot, the fabric of the casting slipper being sufficiently resilient to substantially conform to the patient's foot;
   b. a quantity of curable resin sufficient to harden the casting slipper into a foot casting;
   c. a fabric removal sock configured for placement between the barrier envelope and the foot that expedites sliding removal of the intact hardened casting slipper from the patient's foot, and configured for placement around plantar, dorsal and heel surfaces of a patient's foot and lower extremity and extending upwardly from the plantar surface to an open end of the removal sock on the lower extremity above the dorsal surface of the foot, the fabric of the removal sock having a sufficiently low coefficient of friction between itself and the barrier envelope to minimize vacuum formation between the foot and barrier envelope and facilitate removal of the hardened casting slipper, and being sheer or ultra-sheer with a denier of between 10 and 30, and resilient to substantially conform to the patent's foot; and,
   d. the barrier envelope which is configured for mounting over and adjacent to the removal sock, for prevention of adherence of the resin to the removal sock or the patient's foot, the barrier envelope fabricated from a material which is impermeable to resin.

2. The kit of claim 1 additionally comprising an arch strap with a first and second end, where the first end of the strap is affixable to a side of the casting slipper, the strap dimensioned to span transversely over the dorsum of the patient's foot and the second end of the strap removably affixable to the opposing side of the casting slipper.

3. The kit of claim 1 wherein the fabric casting slipper additionally comprises a resilient longitudinally extensible band located around the circumference of the open end of the casting slipper and configured to hold the open end of the casting slipper snuggly against the dorsum and heel of the foot.

4. The kit of claim 1 wherein the casting slipper (c) and curable resin (d) are provided within a resin-impervious pouch.

5. The kit of claim 1 wherein the curable resin (d) is provided in a container separate from the casting slipper (c).

6. A method of creating an intact custom molded impression casting of a patient's foot and foot arch contour comprising the steps of:
   a) first, mounting a fabric removal sock that expedites removal of a hardened casting slipper from the patient's foot around the patient's foot and lower extremity such that the removal sock extends upwardly from a plantar surface of the patient's foot to an open end on the lower extremity above the dorsal surface of the foot the fabric of the removal sock having a sufficiently low coefficient of friction between itself and a subsequently mounted barrier envelope that minimizes vacuum formation between the foot and barrier envelope and facilitates subsequent sliding removal of the hardened casting slipper, and being sheer or ultra-sheer with a denier of between 10 and 30, and resilient to substantially conform to the patent's foot;
   b) second, mounting the barrier envelope over and adjacent to the removal sock, the barrier envelope being impermeable to resin, and prevents adherence of a resin to the removal sock or the patient's foot, the barrier envelope extending upwardly from a plantar surface of the patient's foot to an open end on the lower extremity well above the dorsal surface of the foot;
   c) third, mounting the casting slipper over the barrier envelope on the patient's foot, the casting slipper is a low-cut resilient casting slipper with a medial and a lateral side, and a heel, and having a curable resin impregnated therein;
   d) pulling the casting slipper up into contact with the contour of the patient's foot arch;
   e) manipulating the patient's foot to achieve a desired orientation;

f) hardening the resin in the casting slipper while the patient's foot is in the desired orientation; and g) removing the intact hardened casting slipper from the patient's foot by pulling the casting slipper down at the heel and sliding the casting slipper forward off the foot.

7. The method of claim 6 wherein an arch strap with a first and second end is additionally provided, the first end affixable to a side of the casting slipper and the second end removably affixable to the opposing side of the casting slipper; and affixing the first end of the arch strap to the medial side of the casting slipper and subsequently affixing the second end of the arch strap to the lateral side of the casting slipper, thereby conforming the casting slipper to the contour of the patient's foot arch.

8. The method of claim 6, after the hardening step (f), removing the hardened casting slipper from the patient's foot, and making a foot orthosis using the hardened casting slipper.

9. The method of claim 8 wherein, the foot orthosis is made by placing a casting material inside the hardened casting slipper, allowing the casting material to harden and removing the hardened casting material from inside the casting slipper by cutting the hardened casting slipper downwardly in the area of the heel and downwardly and anteriorly of the opening of the slipper toward the area of the middle toe and bending the medial and lateral sides of the hardened slipper outwardly to barrier the hardened casting material.

* * * * *